United States Patent [19]
Andersen et al.

[11] Patent Number: 5,612,220
[45] Date of Patent: Mar. 18, 1997

[54] ISOLATED DNA MOLECULE ENCODING SPRM-1 PROTEIN

[75] Inventors: Bogi Andersen, La Jolla; Richard V. Pearse, San Diego, both of Calif.; Peter N. Schlegel, New York, N.Y.; Michael G. Rosenfeld, San Diego, Calif.; C. Wayne Bardin, New York, N.Y.

[73] Assignee: The Population Council, Center for Biomedical Research, New York, N.Y.

[21] Appl. No.: 347,826

[22] Filed: Dec. 1, 1994

[51] Int. Cl.$^6$ .............................. C12N 1/00; C12N 5/10; C12N 15/11; C12N 15/63
[52] U.S. Cl. .................. 435/320.1; 435/243; 435/325; 435/367; 435/358; 435/352; 536/23.5
[58] Field of Search .............................. 435/320.1, 240.1, 435/240.2, 243, 252.3, 172.1, 172.3; 536/23.1, 23.5

[56] References Cited

PUBLICATIONS

Verrijzer et al, The EMBO Journal, 1992, vol. 11(13): pp. 4993–5003.
Ringheim, Studies in Family Planning 24(2): 87–99 (1993).
Andersen et al., PNAS USA 90:11084–88 (1993).
Rosenfeld, et al., Genes Dev. 5:897–907 (1991).
Dekker, et al., Nature 362:852–854 (1993).
He, et al., Neuron 7:183–196 (1991).
Voss, et al., Cell 70:527–530 (1992).
World Health Organization, "Challenges in reproductive health research," Biennial Report 1992–1993, pp. 72–76, 129–133.
World Health Organization, "Reproductive health: a key to a brighter future", Biennial Report 1990–1991, Special 20th anniversary issue, 93–96.
World Health Organization, "Annual TEchnical Report", Geneva, 1992, 59–68, 73–75

*Primary Examiner*—Mindy Fleisher
*Assistant Examiner*—Terry A. McKelvey
*Attorney, Agent, or Firm*—Lerner, David, Littenberg, Krumholz & Mentlik

[57] ABSTRACT

Disclosed is a POU transcription factor, Sprm-1 and analogs thereof, DNA molecules encoding the Sprm-1 proteins, and chimeric constructs, vectors and host cells containing the DNA molecules. Also disclosed are methods to identify putative male contraceptive agents. One involves the steps of isolating a DNA regulatory region responsive to Sprm-1, stably transforming a heterologous cell line with a first chimeric DNA construct containing a constitutive promoter capable of functioning in the cell line operably linked to a Sprm-1 DNA and a second chimeric DNA construct containing the DNA regulatory region operably linked to a reporter gene. The thus-transformed cell line is cultural in media containing the compound so that the thus-cultured cell line can be assayed to determine the Sprm-1 inhibitory activity of the compound. The above method can be modified to evaluate the Sprm-1 inhibitory activity of DNA molecules of interest, by transiently transfecting the thus-transformed cell line with a third DNA construct containing a constitutive promoter capable of functioning in the cell line operably linked to the DNA molecule, and then culturing the thus-transfected cell line so that it can be assayed to determine the inhibitory activity of the DNA molecule. Antibodies specific to Sprm-1, and their use in diagnosing male germ cell Sprm-1-mediated diseases or conditions are further disclosed.

10 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 335 amino acids
        ( B ) TYPE: amino acid
        ( D ) TOPOLOGY: linear ( x i ) SEQUENCE DESCRIPTION: SEQ ID NO:1:

```
Met Ala Gly Arg Arg Ser Ser Asn Val Cys Pro Phe Pro Gly Asn Ser
 1               5                  10                  15
Gly Gly Gly Leu Glu Gly Pro Val Pro Met Arg Val Asp Thr Pro Thr
            20                  25                  30
```

| | | | | | | | | | | | | | | |
|---|---|---|---|---|---|---|---|---|---|---|---|---|---|---|
| Trp | Leu | Ser 35 | Ser | Gln | Ala | Ala | Thr 40 | Ser | Arg | Leu | Met | Val 45 | Arg | Pro | Gly |
| Met | Gly 50 | Pro | Gly | Phe | Cys 55 | Pro | Gly | Pro | Glu | Val | Trp 60 | Gly | Val | Pro | Leu |
| Gly 65 | Pro | Ser | Pro | Tyr | Glu 70 | Phe | Arg | Gly | Gly | Ile 75 | Ala | Pro | Tyr | Gly | Ala 80 |
| Tyr | Glu | Thr | Arg | Thr 85 | Trp | Ser | Gln | Asn | Ser 90 | Ser | Glu | Asp | Thr | Tyr 95 | Pro |
| Gly | Pro | Tyr | Ile 100 | Ala | Leu | Arg | Tyr | Met 105 | Pro | Asn | Leu | Ala | Leu 110 | Pro | Glu |
| Asp | Val | Ser 115 | Ala | Ile | Gln | Lys | Glu 120 | Met | Glu | Gln | Leu | Ala 125 | Lys | Glu | Leu |
| Arg | Gln 130 | Lys | Arg | Met | Thr | Leu 135 | Gly | Tyr | Thr | Gln | Ala 140 | Asp | Val | Gly | Phe |
| Ala 145 | Val | Gly | Ala | Met | Phe 150 | Gly | Lys | Val | Leu | Ser 155 | Gln | Thr | Thr | Ile | Cys 160 |
| Arg | Phe | Glu | Ala | Gln 165 | Gln | Leu | Ser | Leu | Ala 170 | Asn | Met | Trp | Lys | Leu 175 | Arg |
| Pro | Leu | Leu | Lys 180 | Met | Trp | Leu | Glu | Glu 185 | Val | Asp | Glu | Lys | Asn 190 | Leu | Leu |
| Gly | Ile | Ser 195 | Arg | Met | Glu | Met | Ile 200 | Leu | Gln | Gln | Ala | Arg 205 | Lys | Arg | Arg |
| Arg | Ala 210 | Ser | Arg | Glu | Arg | Arg 215 | Ile | Gly | Ser | Asn | Leu 220 | Glu | Lys | Leu | Phe |
| Leu 225 | Gln | Cys | Pro | Glu | Pro 230 | Thr | Pro | Gln | Gln | Ile 235 | Ser | Tyr | Ile | Ala | Gly 240 |
| Arg | Leu | Arg | Leu | Gln 245 | Lys | Asp | Leu | Val | Gln 250 | Val | Trp | Phe | Ser | Asn 255 | Arg |
| Ser | Gln | Met | Ala 260 | Gly | Trp | Pro | Thr | Asn 265 | Asp | Ser | Ser | Gln | Arg 270 | Glu | Asn |
| Val | Gly | Ala 275 | Thr | Gly | Ala | Pro | Phe 280 | Pro | Gly | Pro | Pro | Val 285 | Cys | Phe | Pro |
| Leu | Ala 290 | Pro | Gly | Leu | His | Phe 295 | Asp | Phe | Pro | His | Tyr 300 | Gly | Gly | Ser | Cys |
| Leu 305 | Thr | Pro | Leu | Tyr | Ser 310 | Ser | Thr | Pro | Phe | Pro 315 | Val | Arg | Gln | Ala | Leu 320 |
| Leu | Ser | Ala | Pro | Thr 325 | Thr | Thr | Leu | Gly | Leu 330 | Pro | Arg | Leu | Ser | Ser 335 | |

( 2 ) INFORMATION FOR SEQ ID NO:2:

( i ) SEQUENCE CHARACTERISTICS:
        ( A ) LENGTH: 334 amino acids
        ( B ) TYPE: amino acid
        ( D ) TOPOLOGY: linear ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ala | Gly | Arg | Arg 5 | Ser | Ser | Asn | Val | Phe 10 | Pro | Leu | Ser | Gly | Asn 15 | Ser |
| Gly | Gly | Gly | Leu 20 | Glu | Gly | Pro | Val | Pro 25 | Met | Arg | Val | Asp | Thr 30 | Pro | Thr |
| Trp | Leu | Ser 35 | Ser | Gln | Ala | Ala | Thr 40 | Ser | Arg | Leu | Met | Val 45 | Arg | Pro | Ser |
| Met | Gly 50 | Pro | Gly | Ile | Cys 55 | Pro | Gly | Pro | Glu | Val 60 | Trp | Gly | Val | Pro | Leu |
| Gly | Pro | Ser | Pro | Tyr | Glu | Phe | Arg | Gly | Gly | Ile | Ala | Pro | Tyr | Arg | Ala |

|  |  |  |  |  |  |  |  |  |  |  |  |  |  |  |  |
|---|---|---|---|---|---|---|---|---|---|---|---|---|---|---|---|
| 65 | | | | 70 | | | | 75 | | | | 80 | | | |
| Cys | Glu | Ala | Arg | Arg | Trp | Ser | Gln | Ser | Ser | Glu | Asp | Thr | Cys | Pro | |
| | | | | 85 | | | | 90 | | | | 95 | | | |
| Gly | Pro | Tyr | Ile | Ala | Leu | Arg | Tyr | Met | Pro | Asn | Leu | Ala | Leu | Pro | Glu |
| | | | 100 | | | | | 105 | | | | 110 | | | |
| Asp | Val | Ser | Ala | Ile | Gln | Lys | Glu | Met | Glu | Gln | Leu | Ala | Lys | Glu | Leu |
| | | 115 | | | | | 120 | | | | | 125 | | | |
| Arg | Gln | Lys | Arg | Met | Thr | Leu | Gly | Tyr | Thr | Gln | Ala | Asp | Val | Gly | Phe |
| | 130 | | | | | 135 | | | | | 140 | | | | |
| Ala | Val | Gly | Ala | Met | Phe | Gly | Lys | Val | Leu | Ser | Gln | Thr | Thr | Ile | Cys |
| 145 | | | | | 150 | | | | | 155 | | | | | 160 |
| Arg | Phe | Glu | Ala | Gln | Gln | Leu | Ser | Leu | Ala | Asn | Met | Trp | Lys | Leu | Arg |
| | | | | 165 | | | | | 170 | | | | | 175 | |
| Pro | Leu | Leu | Lys | Met | Trp | Leu | Glu | Glu | Val | Asp | Glu | Lys | Asn | Leu | Leu |
| | | | 180 | | | | | 185 | | | | | 190 | | |
| Gly | Ile | Ser | Arg | Met | Glu | Met | Ile | Leu | Gln | Gln | Ala | Arg | Lys | Arg | Arg |
| | | | 195 | | | | | 200 | | | | | 205 | | |
| Arg | Ala | Ser | Arg | Glu | Arg | Arg | Ile | Gly | Ser | Asn | Leu | Glu | Lys | Leu | Phe |
| | 210 | | | | | 215 | | | | | 220 | | | | |
| Leu | Gln | Cys | Pro | Glu | Pro | Thr | Pro | Gln | Gln | Ile | Ser | Tyr | Ile | Ala | Gly |
| 225 | | | | | 230 | | | | | 235 | | | | | 240 |
| Arg | Leu | Arg | Leu | Gln | Lys | Asp | Leu | Val | Gln | Val | Trp | Phe | Ser | Asn | Arg |
| | | | | 245 | | | | | 250 | | | | | 255 | |
| Ser | Gln | Met | Gly | Ser | Trp | Pro | Thr | Asn | Thr | Ser | Ser | Gly | Glu | Asp | Val |
| | | | 260 | | | | | 265 | | | | | 270 | | |
| Gly | Ala | Thr | Gly | Ala | Pro | Phe | Pro | Phe | Pro | Pro | Val | Cys | Phe | Pro | Leu |
| | | 275 | | | | | 280 | | | | | 285 | | | |
| Ala | Pro | Gly | Leu | His | Phe | Asp | Phe | Pro | His | Tyr | Gly | Gly | Ser | Cys | Leu |
| | 290 | | | | | 295 | | | | | 300 | | | | |
| Thr | Pro | Leu | Tyr | Ser | Ser | Ser | Pro | Phe | Pro | Val | Arg | Gln | Ala | Phe | Leu |
| 305 | | | | | 310 | | | | | 315 | | | | | 320 |
| Ser | Ala | Pro | Thr | Thr | Thr | Leu | Gly | Leu | Pro | Arg | Leu | Ser | Ser | | |
| | | | | 325 | | | | | 330 | | | | | | |

( 2 ) INFORMATION FOR SEQ ID NO:3:

( i ) SEQUENCE CHARACTERISTICS:
        ( A ) LENGTH: 1008 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | |
|---|---|---|---|---|---|
| ATGGCCGGGC | GCAGGTCTTC | AAACGTCTGC | CCCTTCCCAG | GCAATAGTGG | TGGTGGTCTG | 60 |
| GAAGGGCCAG | TTCCCATGCG | AGTTGATACC | CCAACCTGGT | TGAGCAGCCA | GGCAGCCACA | 120 |
| AGCAGGTTAA | TGGTACGGCC | AGGTATGGGG | CCAGGCTTCT | GTCCAGGCCC | TGAGGTATGG | 180 |
| GGAGTGCCTC | TGGGTCCCTC | ACCTTATGAA | TTCCGAGGTG | GGATAGCACC | CTACGGAGCT | 240 |
| TATGAGACAA | GGACCTGGTC | CCAGAATTCC | TCTGAGGATA | CCTACCCAGG | ACCCTACATC | 300 |
| GCCTTAAGGT | ACATGCCAAA | TTTGGCACTG | CCAGAGGATG | TTTCAGCCAT | ACAGAAAGAG | 360 |
| ATGGAGCAGC | TGGCCAAGGA | GCTGAGACAG | AAGAGGATGA | CCCTGGGATA | CACACAGGCC | 420 |
| GATGTGGGAT | TCGCTGTGGG | AGCTATGTTT | GGGAAGGTTC | TCAGCCAGAC | GACCATATGC | 480 |
| CGCTTCGAGG | CCCAGCAGCT | CAGCCTTGCC | AACATGTGGA | AGCTGCGACC | CCTGCTGAAA | 540 |
| ATGTGGTTAG | AGGAAGTAGA | TGAGAAGAAC | CTTCTGGGCA | TATCGAGAAT | GGAGATGATC | 600 |

```
CTGCAGCAGG  CCCGGAAGCG  GAGACGAGCA  AGCAGAGAGA  GACGCATTGG  GAGCAATCTG      660

GAAAAACTGT  TCTTGCAGTG  TCCAGAGCCT  ACGCCCAGC   AAATCAGCTA  TATTGCTGGG      720

CGCCTCCGTC  TGCAGAAGGA  CTTGGTCCAA  GTGTGGTTTT  CTAACCGGAG  CCAGATGGCT      780

GGTTGGCCAA  CCAATGATTC  CTCCCAGAGG  GAGAATGTGG  GGGCAACTGG  GGCCCCTTTC      840

CCAGGGCCAC  CAGTGTGCTT  TCCCCTGGCA  CCAGGGCTCC  ATTTTGATTT  CCCCCACTAT      900

GGGGGGTCAT  GTCTTACACC  CCTGTACTCC  TCTACACCAT  TTCCTGTACG  AGGAGCCCTT      960

TTGTCTGCCC  CAACCACCAC  CCTGGGCCTT  CCCAGGCTGT  CAAGCTGA                   1008
```

(2) INFORMATION FOR SEQ ID NO:4:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (xi) SEQUENCE DESCRIPTION: SEQ ID NO:4:

```
ATGGCCGGGC  GGAGGTCTTC  AAACGTCTTC  CCTCTCTCAG  GCAATAGTGG  TGGTGGCCTG       60

GAAGGGCCAG  TTCCCATGCG  AGTTGACACC  CCAACATGGT  TGAGCAGCCA  GGCAGCCACA      120

AGCAGATTAA  TGGTACGACC  AAGTATGGGT  CCAGGCATCT  GTCCAGGCCC  TGAGGTATGG      180

GGAGTGCCTC  TGGGTCCCTC  ACCTTATGAA  TTCGAGGTG   GGATAGCACC  CTACAGAGCT      240

TGTGAGGCAA  GGGCCTGGTC  CCAGAGTTCC  TCTGAGGATA  CCTGCCCAGG  ACCTTACATC      300

GCCTTGAGAT  ACATGCCAAA  TTTGGCACTG  CCAGAGGACG  TTTCAGCCAT  ACAGAAAGAG      360

ATGGAGCAGC  TAGCCAAGGA  ACTGAGACAG  AAGAGGATGA  CCCTGGGATA  CACACAGGCC      420

GATGTGGGAT  TCGCTGTGGG  AGCTATGTTT  GGGAAGGTTC  TCAGCCAGAC  GACCATATGC      480

CGCTTCGAGG  CCCAGCAGCT  CAGCCTTGCC  AACATGTGGA  AGCTGCGACC  CCTGCTGAAA      540

ATGTGGTTAG  AGGAAGTAGA  TGAGAAGAAC  CTTCTGGGCA  TATCGAGAAT  GGAGATGATC      600

CTGGAGCAGG  CCCGGAAGCG  GAGACGTGCA  AGCAGAGAGA  GACGCATTGG  GAGCAATCTG      660

GAAAAACTGT  TCTTGCAATG  TCCAGAGCCT  ACGCCCAGC   AAATCAGCTA  TATTGCTGGG      720

CGCCTCCGGC  TGCAGAAAGA  CCTGGTCCAA  GTGTGGTTTT  CTAACCGGAG  CCAGATGGGC      780

AGTTGGCCAA  CCAATGATAC  CTCCGGGGAG  GATGTGGGGG  CAACTGGGTC  TCCTTTCCCA      840

GGTCCACCAG  TGTGCTTTCC  CATGGCACCA  GGGCTCCATT  TTGATTTCCC  CCACTATGAG      900

GGATCATGTC  TTACACCCCT  GTACTCCTCT  ACATCCTTTC  CTGTACGAGG  AGCCTTTTTG      960

TCTGCCCCAA  CCACCACTCT  GGGCCTTCCC  AGGCTGTCAA  GCTGA                     1005
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

```
TAGAATTCAR  WSNACNATHW  SNMGNTT YGA                                         30
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single ( D ) TOPOLOGY: linear ( x i ) SEQUENCE DESCRIPTION: SEQ ID NO:6:

TAGGATCCTG NSDNYKRTTR CARAACCANA C    31

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AAGGGGATCC AAATGTCAAT TAAATATCAA    30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCCTCATTAG TGATATTTAC CTCCAAATGC    30

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTGAAAATA TGTGTAATAT GTAAACATT TTG    33

( 2 ) INFORMATION FOR SEQ ID NO:10:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGATGAATTC CTAAGCGCAT NNNNNNNNGA GCTCAGATCT C    41

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CGATGAATTC CTAAG    15

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

ACGAGATCTG AGCTC 15

( 2 ) INFORMATION FOR SEQ ID NO:13:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATGCWAAT 8

( 2 ) INFORMATION FOR SEQ ID NO:14:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 7
        ( D ) OTHER INFORMATION: /note="+or −N"

( x i ) SEQUENCE DESCRIPTION: SEQ ID NO:14:

GCATNNNTAA T 11

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCATATGTTA AT 12

ISOLATED DNA MOLECULE ENCODING SPRM-1 PROTEIN

FIELD OF THE INVENTION

The invention relates to the fields of developmental regulation, cell differentiation and male contraception.

BACKGROUND OF THE INVENTION

Modern family planning depends on the availability of contraceptive methods. At present, the major burden of fertility regulation is carried by women since most available methods are female methods. Oral contraceptives, implants and injectables intrauterine devices, tubal ligation, diaphrams, and spermicides are all methods practiced by females.

Methods for controlling male fertility have been known for centuries, but social science research on such methods has existed for only about twenty years, coinciding roughly with the widespread introduction of vasectomy. See Ringheim, Studies In Family Planning 24(2): 87–99 (1993). Currently available methods, however, have several drawbacks. For example, although vasectomy is one of the most prevalent methods in the United States, Australia, and New Zealand, it remains little used elsewhere, partially because the difficulty and expense of reversal still limit the appropriateness of the technique to those wishing to stop rather than space child bearing, and the method's irreversibility remains the biggest obstacle to its acceptability. Id. The vas occlusion method utilizing a silicone plug, and other methods of occluding the vas that are currently undergoing clinical trials may only be somewhat more acceptable than vasectomy, unless they are easily reversible. Id. The slow progress in the development of male contraceptives has been due in part to the relative complexity of the male reproductive system. Id.

Evidence is forthcoming that a drug-based male contraceptive would be acceptable in many countries. However, controlling male reproduction by interfering with the spermatogenic process has been a much more difficult task to achieve than inhibiting ovalation. See World Health Organization, "Challenges in reproductive health research," Biennial Report 1992–1993. In particular, research has focused on a selection of a variety of hormonal drugs that can effectively suppress pituitary hormone secretion. For instance, several small trials involving GnRH antagonists have provided evidence that these drugs effectively suppress the release of gonadotrophins and render a significant proportion of men azoospermic (i.e., the complete absence of sperm from the ejaculate). However, the current generation of antagonists do not have sufficient biological potency and thus can not be considered for further development, since in order to attain the desired level of efficacy too much compound will be needed, which will be to expensive. Id. A number of substances are also known to effect male fertility via a direct interference with the process of spermatogenesis. Unfortunately, research on most of the substances has not gone beyond pre clinical studies because of toxicity or because undesirable side-effects were observed in animals. Id.

In view of the readiness of men to accept new male contraceptive methods is underlined by repeated opinion polls. See, e.g., Konig U., Revolution bei der Verhutung: J etzt sind die Manner dran. Stern 24/91:28–34 (1991). Research to develop safe, effective, reversible and acceptable methods of fertility regulation for men has thus been supported by several international agencies, many national research counsels, and some pharmaceutical companies. Accordingly, not only a long-term need remains not only for the development of safe and effective male contraceptives, but also a short term need for the development of a means to screen large numbers of substances to identify and evaluate potential contraceptive agents.

Spermatogenesis is a terminal differentiation process whereby male germ cells develop into mature spermatozoa. Leblond, et al., Ann. N.Y. Acad. Sci. 55:548–573 (1952); Parvinen, M., Endocr. Rev. 3:404–417 (1982). Primordial germ cells, derived from primitive ectoderm, are established in the primitive gonad on embryonic day 10.5 in the mouse. After birth these cells proliferate extensively giving rise to type A spermatogonia which can either replicate as stem cells or differentiate to type B spermatogonia. At puberty type B spermatogonia develop into large diploid primary spermatocytes that undergo two reductive divisions, giving rise to the haploid spermatids. Spermatids evolve into mobile spermatozoa through a process referred to as spermiogenesis, characterized by restructuring of their nuclei and development of flagella. An essential component of spermiogenesis is meiosis, a process that involves a single round of DNA replication, pairing and recombination, followed by two reductive divisions. See Parvinen, supra. Although meiotic reduction has been extensively studied in yeast (reviewed in McLeod, BioAssays 11:9–14(1989), much less is known of the regulatory factors that may be involved in meiosis in mammals.

Molecular cloning of the mammalian DNA-binding proteins Oct-1, Oct-2 and Pit-1, and the *C. elegans* developmental regulatory gene unc-86, revealed that all had a common sequence referred to as the POU-domain, which is required for high affinity DNA-binding and protein-protein interactions. Herr, et al., Genes Dev. 2:1513–1516 (1988). The POU-domain is a bipartite structure comprised of the POU-specific domain, which is connected by a short variable linker sequence to the POU homeodomain. Subsequently, several new members of this gene family, most of which are predominantly expressed in the developing and adult nervous system, have been described in mammals. See Ruvkun, et al., Cell 64:475–478 (1991); Rosenfeld, et al., Genes Dev. 5:897–907 (1991); and Scholer, Trends Genes. 7:323–329 (1991). Notable exceptions to this expression pattern are provided by Oct-1, Sturm, et al., Genes Dev. 2:1582–1599 (1988); and Brn-5, Andersen, et al., Biol. Chem. 268, in press (1993) that have widespread distribution; Pit-1, Oct-2 and Skn-1a/i that are expressed in the anterior pituitary, Ingraham, et al., Cell 55:519–529 (1988); B lymphocytes, Clerc, et al., Genes Dev. 2:1570–1582 (1988), and skin, Andersen, et al., Science 260:78–82 (1993), respectively; and Oct-3/4 that is expressed in undifferentiated cells early in development and later becomes restricted to oocytes, Okamoto, et al., Cell 60:461–472 (1990); Scholer, et al., Nature (London) 344:435–439 (1990); Rosner, et al., Nature (London) 345:686–692 (1990); and Scholer, et al., EMBO J. 9:2185–2195 (1990).

Genetic evidence indicates that Oct-2, Pit-1 and unc-86 are required for cell determination and/or function in B lymphocytes (Corcoran, et al., Genes Dev. 7:570–582 (1993)), anterior pituitary (Li, et al., Nature (London) 347:528–533 (1990)), and sensory neurons (Finney, et al., Cell 63:895–905 (1990)). Although the functions of other POU proteins remain elusive, the present evidence suggests that many members of this family may have important roles in cell specification and terminal differentiation.

SUMMARY OF THE INVENTION

In one embodiment according to the present invention, a POU transcription factor, Sprm-1, and analogs thereof are provided. In another embodiment, DNA molecules encoding the Sprm-1 proteins, and chimeric constructs, vectors and host cells containing the DNA molecules are provided.

In yet another embodiment, Sprm-1 encoding DNAs are used in a method to identify putative male contraceptive agents. The method involves the steps of:

a) isolating a DNA regulatory region responsive to Sprm-1;

b) stably transforming a heterologous cell line with a first chimeric DNA construct containing a constitutive promoter capable of functioning in the cell line operably linked to a Sprm-1 DNA and a second chimeric DNA construct containing the DNA regulatory region operably linked to a reporter gene; and c) culturing the thus-transformed cell line in media containing the compound so that the thus-cultured cell line can be assayed to determine the Sprm-1 inhibitory activity of the compound.

The above method can be modified to evaluate the Sprm-1 inhibitory activity of DNA molecules of interest by transiently transfecting the thus-transformed cell line with a third DNA construct containing a constitutive promoter capable of functioning in the cell line operably linked to the DNA molecule, and then culturing the thus-transfected cell line so that it can be assayed to determine the inhibitory activity of the DNA molecule.

A further embodiment of the present invention is directed to antibodies specific to Sprm-1, and their use in diagnosing male germ cell Sprm-1-mediated diseases or conditions. Such methods involve the steps of obtaining a biopsy of testicular fluid from a patient, analyzing the tissue with a primary antibody which is specific to Sprm-1, and then adding to the thus-analyzed biopsied tissue a secondary antibody which is capable of binding to the anti-Sprm-1 antibody so that Sprm-1 immunoreactivity could be detected. Detection of Sprm-1 immunoreactivity is preferably carried out via immunoassay or immunostaining techniques.

DETAILED DESCRIPTION OF THE PREFERRED EMBODIMENTS

The disclosed Sprm-1 protein is a POU-domain transcription factor. Andersen et al., PNAS USA 90:11084–88 (1993), incorporated herein by reference in its entirety. These proteins have been implicated in transcriptional regulation, development and cell differentiation. See, e.g., Dekker et al., Nature 362:852–854 (1993); Rosenfeld, Genes & Development 5:897–907 (1991). These proteins typically contain a bipartite DNA-binding domain composed of a POU-specific domain ($POU_s$) and a POU-homeodomain ($POU_{hd}$) connected by a flexible linker. Id. The amino acid sequences of rat and mouse Sprm-1 proteins are set forth below in Table I as SEQ ID NOS: 1 and 2, respectively. Turning to SEQ ID NO: 1 (the top row), the POU-specific domain includes amino acid residues 117 (Ile)-186 (Val), inclusive. This domain is linked to the POU-homeodomain, i.e., amino acid residues 205 (Arg)-262 (Trp)) via a linker which contains amino acid residues 187 (Asp)-204 (Ala).

TABLE I

| | | | | | | | | | (10) | |
|---|---|---|---|---|---|---|---|---|---|---|
| 5' Met | Ala | Gly | Arg | Arg | Ser | Ser | Asn | Val | Cys | (SEQ ID NO: 1) |
| Met | Ala | Gly | Arg | Arg | Ser | Ser | Asn | Val | Phe | (SEQ ID NO: 2) |
| | | | | | | | | | (20) | |
| Pro | Phe | Pro | Gly | Asn | Ser | Gly | Gly | Gly | Leu | Glu |
| Pro | Leu | Ser | Gly | Asn | Ser | Gly | Gly | Gly | Leu | Glu |
| | | | | | | | | (30) | | |
| Gly | Pro | Val | Pro | Met | Arg | Val | Asp | Thr | Pro | Thr |
| Gly | Pro | Val | Pro | Met | Arg | Val | Asp | Thr | Pro | Thr |
| | | | | | | | (40) | | | |
| Trp | Leu | Ser | Ser | Gln | Ala | Ala | Thr | Ser | Arg | Leu |
| Trp | Leu | Ser | Ser | Gln | Ala | Ala | Thr | Ser | Arg | Leu |
| | | | | | | (50) | | | | |
| Met | Val | Arg | Pro | Gly | Met | Gly | Pro | Gly | Phe | Cys |
| Met | Val | Arg | Pro | Ser | Met | Gly | Pro | Gly | Ile | Cys |
| | | | | | (60) | | | | | |
| Pro | Gly | Pro | Glu | Val | Trp | Gly | Val | Pro | Leu | Gly |
| Pro | Gly | Pro | Glu | Val | Trp | Gly | Val | Pro | Leu | Gly |
| | | | | (70) | | | | | | |
| Pro | Ser | Pro | Tyr | Glu | Phe | Arg | Gly | Gly | Ile | Ala |
| Pro | Ser | Pro | Glu | Glu | Phe | Arg | Gly | Gly | Ile | Ala |
| | | | (80) | | | | | | | |
| Pro | Tyr | Gly | Ala | Tyr | Glu | Thr | Arg | Thr | Trp | Ser |
| Pro | Tyr | Arg | Ala | Cys | Glu | Ala | Arg | Arg | Trp | Ser |
| | | (90) | | | | | | | | |
| Gln | Asn | Ser | Ser | Glu | Asp | Thr | Tyr | Pro | Gly | Pro |
| Gln | Ser | Ser | Ser | Glu | Asp | Thr | Cys | Pro | Gly | Pro |
| | (100) | | | | | | | | | |
| Tyr | Ile | Ala | Leu | Arg | Tyr | Met | Pro | Asn | Leu | Ala |
| Tyr | Ile | Ala | Leu | Arg | Tyr | Met | Pro | Asn | Leu | Ala |
| (110) | | | | | | | | | | (120) |
| Leu | Pro | Glu | Asp | Val | Ser | Ala | Ile | Gln | Lys | Glu |
| Leu | Pro | Glu | Asp | Val | Ser | Ala | Ile | Gln | Lys | Glu |

| | | | | | | | | (130) | |
|---|---|---|---|---|---|---|---|---|---|
| Met | Glu | Gln | Leu | Ala | Lys | Glu | Leu | Arg | Gln | Lys |
| Met | Glu | Gln | Leu | Ala | Lys | Glu | Leu | Arg | Gln | Lys |

| | | | | | (140) | | | | |
|---|---|---|---|---|---|---|---|---|---|
| Arg | Met | Thr | Leu | Gly | Tyr | Thr | Gln | Ala | Asp | Val |

TABLE I-continued

| | | | | | | | | | |
|---|---|---|---|---|---|---|---|---|---|
| Arg | Met | Thr | Leu | Gly | Tyr | Thr | Gln | Ala | Asp | Val |

| | | | | | | (150) | | | |
|---|---|---|---|---|---|---|---|---|---|
| Gly | Phe | Ala | Val | Gly | Ala | Met | Phe | Gly | Lys | Val |
| Gly | Phe | Ala | Val | Gly | Ala | Met | Phe | Gly | Lys | Val |

| | | | | | (160) | | | | |
|---|---|---|---|---|---|---|---|---|---|
| Leu | Ser | Gln | Thr | Thr | Ile | Cys | Arg | Phe | Glu | Ala |
| Leu | Ser | Gln | Thr | Thr | Ile | Cys | Arg | Phe | Glu | Ala |

| | | | | (170) | | | | | |
|---|---|---|---|---|---|---|---|---|---|
| Gln | Gln | Leu | Ser | Leu | Ala | Asn | Met | Trp | Lys | Leu |
| Gln | Gln | Leu | Ser | Leu | Ala | Asn | Met | Try | Lys | Leu |

| | | | (180) | | | | | | |
|---|---|---|---|---|---|---|---|---|---|
| Arg | Pro | Leu | Leu | Lys | Met | Trp | Leu | Glu | Glu | Val |
| Arg | Pro | Leu | Leu | Lys | Met | Trp | Leu | Glu | Glu | Val |

| | | | (190) | | | | | | |
|---|---|---|---|---|---|---|---|---|---|
| Asp | Glu | Lys | Asn | Leu | Leu | Gly | Ile | Ser | Arg | Met |
| Asp | Glu | Lys | Asn | Leu | Leu | Gly | Ile | Ser | Arg | Met |

| | | (200) | | | | | | | |
|---|---|---|---|---|---|---|---|---|---|
| Glu | Met | Ile | Leu | Gln | Gln | Ala | Arg | Lys | Arg | Arg |
| Glu | Met | Ile | Leu | Gln | Gln | Ala | Arg | Lys | Arg | Arg |

| | (210) | | | | | | | | |
|---|---|---|---|---|---|---|---|---|---|
| Arg | Ala | Ser | Arg | Glu | Arg | Arg | Ile | Gly | Ser | Asn |
| Arg | Ala | Ser | Arg | Glu | Arg | Arg | Ile | Gly | Ser | Asn |

| (220) | | | | | | | | | (230) |
|---|---|---|---|---|---|---|---|---|---|
| Leu | Glu | Lys | Leu | Phe | Leu | Gln | Cys | Pro | Glu | Pro |
| Leu | Glu | Lys | Leu | Phe | Leu | Gln | Cys | Pro | Glu | Pro |

| | | | | | | | | (240) | |
|---|---|---|---|---|---|---|---|---|---|
| Thr | Pro | Gln | Gln | Ile | Ser | Tyr | Ile | Ala | Gly | Arg |
| Thr | Pro | Gln | Gln | Ile | Ser | Tyr | Ile | Ala | Gly | Arg |

| | | | | | | | (250) | | |
|---|---|---|---|---|---|---|---|---|---|
| Leu | Arg | Leu | Gln | Lys | Asp | Leu | Val | Gln | Val | Trp |
| Leu | Arg | Leu | Gln | Lys | Asp | Leu | Val | Gln | Val | Try |

| | | | | | (260) | | | | |
|---|---|---|---|---|---|---|---|---|---|
| Phe | Ser | Asn | Arg | Ser | Gln | Met | Ala | Gly | Trp | Pro |
| Phe | Ser | Asn | Arg | Ser | Gln | Met | Gly | Ser | Try | Pro |

| | | | | | (270) | | | | |
|---|---|---|---|---|---|---|---|---|---|
| Thr | Asn | Asp | Ser | Ser | Gln | Arg | Glu | Asn | Val | Gly |
| Thr | Asn | Thr | Ser | Ser | Gly | | Glu | Asp | Val | Gly |
| | | | | | (280) | | | | |
| Ala | Thr | Gly | Ala | Pro | Phe | Pro | Gly | Pro | Pro | Val |
| Ala | Thr | Gly | Ala | Pro | Phe | Pro | Phe | Pro | Pro | Val |
| | | | | (290) | | | | | |
| Cys | Phe | Pro | Leu | Ala | Pro | Gly | Leu | His | Phe | Asp |
| Cys | Phe | Pro | Leu | Ala | Pro | Gly | Leu | His | Phe | Asp |
| | | | (300) | | | | | | |
| Phe | Pro | His | Tyr | Gly | Gly | Ser | Cys | Leu | Thr | Pro |
| Phe | Pro | His | Tyr | Gly | Gly | Ser | Cys | Leu | Thr | Pro |
| | | (310) | | | | | | | |
| Leu | Tyr | Ser | Ser | Thr | Pro | Phe | Pro | Val | Arg | Gln |
| Leu | Tyr | Ser | Ser | Ser | Pro | Phe | Pro | Val | Arg | Gln |
| | (320) | | | | | | | | |
| Ala | Leu | Leu | Ser | Ala | Pro | Thr | Thr | Thr | Leu | Gly |
| Ala | Phe | Leu | Ser | Ala | Pro | Thr | Thr | Thr | Leu | Gly |
| (330) | | | | | | | | | |
| Leu | Pro | Arg | Leu | Ser | Ser | | | | | |
| Leu | Pro | Arg | Leu | Ser | Ser | 3' | | | | |

The mouse Sprm-1 amino acid sequence shares a significant homology, i.e., about 93%, with the rat sequence. The corresponding POU-specific domain, POU-homeodomain and the corresponding linker are underscored. To identify and isolate other mammalian Sprm-1 proteins such as human Sprm-1 protein, corresponding DNA, e.g., cDNA, libraries can be prepared and then screened with appropriately labelled mouse and/or rat cDNA probes. These probes may be designed to correspond to highly conserved regions of the rat and mouse Sprm-1-encoding DNAs. The corresponding cDNAs encoding the rat and mouse Sprm-1 proteins are set forth in Table II as SEQ ID NOS: 3 and 4, respectively. Those skilled in the art will be able to design such probes on the basis of conserved regions in these sequences.

TABLE II

| | | | | | | | | | (30) | |
|---|---|---|---|---|---|---|---|---|---|---|
| 5' ATG | GCC | GGG | CGC | AGG | TCT | TCA | AAC | GTC | TGC | (SEQ ID NO: 3) |
| ATG | GCC | GGG | CGG | AGG | TCT | TCA | AAC | GTC | TTC | (SEQ ID NO: 4) |
| | | | | | | | | | (60) | |
| CCC | TTC | CCA | GGC | AAT | AGT | GGT | GGT | GGT | CTG | GAA |
| CCT | CTC | TCA | GGC | AAT | AGT | GGT | GGT | GGC | CTG | GAA |
| | | | | | | | | (90) | | |
| GGG | CCA | GTT | CCC | ATG | CGA | GTT | GAT | ACC | CCA | ACC |
| GGG | CCA | GTT | CCC | ATG | CGA | GTT | GAC | ACC | CCA | ACA |
| | | | | | | | (120) | | | |
| TGG | TTG | AGC | AGC | CAG | GCA | GCC | ACA | AGC | AGG | TTA |
| TGG | TTG | AGC | AGC | CAG | GCA | GCC | ACA | AGC | AGA | TTA |
| | | | | | | (150) | | | | |
| ATG | GTA | CGG | CCA | GGT | ATG | GGG | CCA | GGC | TTC | TGT |
| ATG | GTA | CGA | CCA | AGT | ATG | GGT | CCA | GGC | ATC | TGT |
| | | | | | (180) | | | | | |
| CCA | GGC | CCT | GAG | GTA | TGG | GGA | GTG | CCT | CTG | GGT |
| CCA | GGC | CCT | GAG | GTA | TGG | GGA | GTG | CCT | CTG | GGT |
| | | | | | (210) | | | | | |
| CCC | TCA | CCT | TAT | GAA | TTC | CGA | GGT | GGG | ATA | GCA |
| CCC | TCA | CCT | TAT | GAA | TTC | CGA | GGT | GGG | ATA | GCA |
| | | | | (240) | | | | | | |
| CCC | TAC | GGA | GCT | TAT | GAG | ACA | AGG | ACC | TGG | TCC |
| CCC | TAC | AGA | GCT | TGT | GAG | GCA | AGG | GCC | TGG | TCC |
| | | | (270) | | | | | | | |
| CAG | AAT | TCC | TCT | GAG | GAT | ACC | TAC | CCA | GGA | CCC |
| CAG | AGT | TCC | TCT | GAG | GAT | ACC | TGC | CCA | GGA | CCT |
| | (300) | | | | | | | | | |
| TAC | ATC | GCC | TTA | AGG | TAC | ATG | CCA | AAT | TTG | GCA |
| TAC | ATC | GCC | TTG | AGA | TAC | ATG | CCA | AAT | TTG | GCA |
| (330) | | | | | | | | | | (360) |
| CTG | CCA | GAG | GAT | GTT | TCA | GCC | ATA | CAG | AAA | GAG |
| CTG | CCA | GAG | GAC | GTT | TCA | GCC | ATA | CAG | AAA | GAG |
| | | | | | | | | | (390) | |
| ATG | GAG | CAG | CTG | GCC | AAG | GAG | CTG | AGA | CAG | AAG |
| ATG | GAG | CAG | CTA | GCC | AAG | GAA | CTG | AGA | CAG | AAG |
| | | | | | | | (420) | | | |
| AGG | ATG | ACC | CTG | GGA | TAC | ACA | CAG | GCC | GAT | GTG |
| AGG | ATG | ACC | CTG | GGA | TAC | ACA | CAG | GCC | GAT | GTG |
| | | | | | | (450) | | | | |
| GGA | TTC | GCT | GTG | GGA | GCT | ATG | TTT | GGG | AAG | GTT |
| GGA | TTC | GCT | GTG | GGA | GCT | ATG | TTT | GGG | AAG | GTT |
| | | | | | (480) | | | | | |
| CTC | AGC | CAG | ACG | ACC | ATA | TGC | CGC | TTC | GAG | GCC |
| CTC | AGC | CAG | ACG | ACC | ATA | TGC | CGC | TTC | GAG | GCC |
| | | | | (510) | | | | | | |
| CAG | CAG | CTC | AGC | CTT | GCC | AAC | ATG | TGG | AAG | CTG |
| CAG | CAG | CTC | AGC | CTT | GCC | AAC | ATG | TGG | AAG | CTG |
| | | | (540) | | | | | | | |
| CGA | CCC | CTG | CTG | AAA | ATG | TGG | TTA | GAG | GAA | GTA |
| CGA | CCC | CTG | CTG | AAA | ATG | TGG | TTA | GAG | GAA | GTA |
| | | (570) | | | | | | | | |
| GAT | GAG | AAG | AAC | CTT | CTG | GGC | ATA | TCG | AGA | ATG |
| GAT | GAG | AAG | AAC | CTT | CTG | GGC | ATA | TCG | AGA | ATG |
| | (600) | | | | | | | | | |
| GAG | ATG | ATC | CTG | CAG | CAG | GCC | CGG | AAG | CGG | AGA |
| GAG | ATG | ATC | CTG | GAG | CAG | GCC | CGG | AAG | CGG | AGA |
| (630) | | | | | | | | | | |
| CGA | GCA | AGC | AGA | GAG | AGA | CGC | ATT | GGG | AGC | AAT |
| CGT | GCA | AGC | AGA | GAG | AGA | CGC | ATT | GGG | AGC | AAT |
| (660) | | | | | | | | | | (690) |
| CTG | GAA | AAA | CTG | TTC | TTG | CAG | TGT | CCA | GAG | CCT |
| CTG | GAA | AAA | CTG | TTC | TTG | CAA | TGT | CCA | GAG | CCT |
| | | | | | | | | | (720) | |
| ACG | CCC | CAG | CAA | ATC | AGC | TAT | ATT | GCT | GGG | CGC |
| ACG | CCC | CAG | CAA | ATC | AGC | TAT | ATT | GCT | GGG | CGC |
| | | | | | | | | (750) | | |
| CTC | CGT | CTG | CAG | AAG | GAC | TTG | GTC | CAA | GTG | TGG |
| CTC | CGG | CTG | CAG | AAA | GAC | CTG | dTC | CAA | GTG | TGG |
| | | | | | | | (780) | | | |
| TTT | TCT | AAC | CGG | AGC | CAG | ATG | GCT | GGT | TGG | ICCA |
| TTT | TCT | AAC | CGG | AGC | CAG | ATG | GGC | AGT | TGG | CCA |
| | | | | | | (810) | | | | |
| ACC | AAT | GAT | TCC | TCC | CAG | AGG | GAG | AAT | GTG | GGG |
| ACC | AAT | GAT | ACC | TCC | GGG | | GAG | GAT | GTG | GGG |
| | | | | | (840) | | | | | |
| GCA | ACT | GGG | GCC | CCT | TTC | CCA | GGG | CCA | CCA | GTG |
| GCA | ACT | GGG | TCT | CCT | TTC | CCA | GGT | CCA | CCA | GTG |
| | | | | (870) | | | | | | |

TABLE II-continued

```
TGC  TTT  CCC  CTG  GCA  CCA  GGG  CTC  CAT  TTT  GAT
TGC  TTT  CCC  ATG  GCA  CCA  GGG  CTC  CAT  TTT  GAT
               (900)
TTC  CCC  CAC  TAT  GGG  GGG  TCA  TGT  CTT  ACA  CCC
TTC  CCC  CAC  TAT  GAG  GGA  TCA  TGT  CTT  ACA  CCC
          (930)
CTG  TAC  TCC  TCT  ACA  CCA  TTT  CCT  GTA  CGA  GGA
CTG  TAC  TCC  TCT  ACA  TCC  TTT  CCT  GTA  CGA  GGA
     (960)
GCC  CTT  TTG  TCT  GCC  CCA  ACC  ACC  ACC  CTG  GGC
GCC  TTT  TTG  TCT  GCC  CCA  ACC  ACC  ACT  CTG  GGC
(990)
CTT  CCC  AGG  CTG  TCA  AGC  TGA  3'
CTT  CCC  AGG  CTG  TCA  AGC  TGA  3'
```

Analogs of mammalian Sprm-1 proteins are also encompassed by the present invention. By the term "analogs," it is meant point mutations, substitutions, additions, and deletions to the native Sprm-1 proteins which do not result in a significant loss of activity of the protein, i.e., on the DNA responsive elements to which the Sprm-1 proteins bind. Active fragments of the Sprm-1 protein will generally include the bi-partite DNA binding domain, i.e., the POU-specific domain and the POU-homeodomain. However, the minimum sequence and those amino acids necessary for activity can be determined by routine methods. These amino acid residues can also be determined by a systematic or random replacement of same with residues of equivalent stearic size, e.g., by site-specific mutagenesis. If the replacement of a particular residue with a residue of equivalent size results in loss of activity, the essential nature of the replaced residue is confirmed. This sort of analysis can be performed on the N-terminal region of the Sprm-1 protein (in the case of rat, amino acid residues 1–116), the C-terminal region (in the case of rat, amino acid residues 262–334), as well as the bi-partite DNA-binding domain.

Sprm-1 protein can be prepared using recombinant DNA techniques known in the art, see, e.g., J. Sambrook et al., "Molecular Cloning; A Laboratory Manual (1989)"; "DNA Cloning", Vol. I and II (D. N. Glover ed. 1985). Both prokaryotic and eukaryotic host cells are useful for expressing desired coding sequences when appropriate control sequences compatible with the designated host are used. Among prokaryotic hosts, E. coli is preferred. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. Other prokaryotic hosts such as strains of Bacillus or Pseudomonas may be used, with corresponding control sequences.

Suitable eukaryotic hosts include yeast and mammalian cells. Yeast expression hosts include Saccharomyces, Klebsiella, Picia, and the like. See Romano et al., Yeast 8: 423–488 (1992); Section IV of Goeddel (Ed.) Meth. Enzymol. 185: 231–484 (1990); and U.S. Pat. No. 4,775,622. Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers et al., Nature (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art as are suitable vectors. See generally Chapter 16, "Expression of Cloned Genes in Mammalian Cells," in Maniatis et al., Molecular Cloning, A Laboratory Manual, Cold Spring Harbor, N.Y. (1989); Moss, in GENE TRANSFER VECTORS FOR MAMMALIAN CELLS (Miller and Calos, eds.), Cold Spring Harbor Laboratory, N.Y., 1987), p.10).

Polyclonal and monoclonal antibodies specific to the Sprm-1 proteins and analogs thereof may be prepared in accordance with standard techniques. Polyclonal antibodies, for example, are raised by injecting the protein into an animal, e.g., rabbit, to raise anti-Sprm-1 antibodies. See, e.g., A. Johnstone and R. Thorpe, Immunochemistry In Practice, Blackwell Scientific Publications, Oxford (1982). Monoclonal antibodies specific to the Sprm-1 proteins of the present invention may be prepared according to the techniques disclosed in Kohler and Milstein, Nature 256:495–97 (1975). See also Peters, J. H., (eds.) Monoclonal Antibodies, Springer Verlag Berlin, Heidelberg, Germany (1992). The anti-Sprm-1 antibodies of the present invention can be used to detect the presence of Sprm-1 in mammalian testis in accordance with standard techniques.

The antibodies of the present invention may also be used as an aid in the diagnosis of Sprm-1-mediated germ cell conditions or diseases, e.g., male infertility, spermatogenic incompetence and germ cell tumors, in accordance with standard techniques. By the term "Sprm-1-mediated," it is meant diseases or conditions mediated by faulty transcriptional or translational aspects of Sprm-1 production. In a preferred immunostaining method, a biopsy of a testicular tissue from a patient is obtained, and then stabilized, e.g., fixed in formalin and then embedded in paraffin or other suitable material. The tissue is then sliced. The sliced biopsy preparation is then analyzed for Sprm-1 immunoreactivity using a primary anti-Sprm-1 antibody, preferably a polyclonal antibody, followed by the addition of a secondary, detectably labelled antibody capable of binding to anti-Sprm-1 antibody. A preferred antibody is goat anti-rabbit Ig, which may be detectably labelled, e.g., with an enzyme such as horseradish peroxidase (HRP). An HRP substrate is added, and the extent of the reaction is indicative of the immunoreactivity of the Sprm-1 in the sample. Alternatively, the biopsied tissue can be homogenized and then subjected to an immunoassay using a primary antibody which is specific to Sprm-1 and a secondary detectably labelled antibody which is capable of binding to anti-Sprm-1 antibody. A variety of labels can be used in these methods, including radio-isotopes, enzymes and fluorescent markers. The lack of Sprm-1 immunoreactivity may be indicative of such disease or condition.

Male infertility can be alternatively diagnosed by obtaining a cell containing fluid sample or a tissue sample from a patient, and isolating DNA therefrom. The gene encoding Sprm-1 is isolated, e.g., by using PCR techniques, followed by sequencing the gene. The sequence of the thus-isolated Sprm-1 gene is then compared with the nucleic acid sequence of Sprm-1 genes isolated from a control group of fertile patients.

The Sprm-1 DNAs (i.e., DNA molecules encoding proteins having Sprm-1 activity) are also used in methods to identify putative male contraceptive agents. While not intending to be bound by any particular theory of operation, applicants believe that the expression of Sprm-1 in testis is a critical factor in the ultimate differentiation of male germ cells, and that in the absence of such expression, male germ cells will not undergo complete spermatogenesis, i.e., they will be unable to fertilize an egg.

To test a non-nucleic acid compound e.g., a hormone, suspected of having inhibitory activity in accordance with this embodiment of the present invention, a DNA regulatory region (e.g., an enhancer or a promoter) responsive to Sprm-1 protein is isolated. This is typically done by preparing total genomic DNA, or via PCR techniques. The thus-isolated region is then cloned upstream of a reporter gene, e.g., a luciferase, so that the reporter gene is under the transcriptional control of the cloned regulatory region. The cell line is stably transformed with the thus-prepared construct along with a second chimeric construct containing a constitutive promoter functional in the cell line operably linked to a Sprm-1 DNA. A preferred cell line is CV-1 (green monkey kidney) cells. However, most non-spermatogenic cell lines can be used. A preferred constitutive promoter is a CMV promoter. The constitutive promoter-Sprm-1 gene chimeric construct can be contained in the same vector containing the isolated DNA regulatory region-reporter gene construct, or in a different vector. The thus-transformed cell line is then cultured under suitable conditions in media containing the compound suspected of having Sprm-1 inhibitory activity. The inhibitory activity of the compound is determined by the extent of expression of the reporter gene.

To practice this embodiment of the present invention with nucleic acids compounds suspected of having Sprm-1 inhibitory activity, a stably transformed heterologous cell line described above is transiently transfected with a third chimeric construct containing a constitutive promoter capable of functioning in the cell line operable linked to the nucleic acid of interest. After a suitable incubation period, e.g., about 3–4 days, the cultured cells are assayed for Sprm-1 inhibitory activity in the same manner as above.

The Sprm-1 proteins of the present invention can also be used in molecular modeling to screen drugs that could block the binding of Sprm-1 to DNA. See Assa-munt et al., Cell 73: 193–205 (1993).

The invention will be further described by reference to the following detailed examples. These examples are provided for purposes of illustration only, and are not intended to be limiting unless otherwise specified.

EXAMPLES

Example 1 cDNA Cloning

Complementary DNA was generated as previously described from several rat tissues from adults and embryos (Andersen, B., et. al., Science 260:78–82 (1993)). This cDNA was used as a template in the polymerase chain reaction (PCR) with degenerate primers corresponding to the third helix of the POU-specific domain [5'oligo:5'TAGAATTCAR WSNACNATHW SNMGNT-TYGA-3'] (SEQ ID NO: 5) and the third helix of the POU homeodomain [3'oligo: 5'TAGGATCCTG NSDNYKRTTR CARAACCANA C-3'] (SEQ ID NO: 6). One of the POU-domains identified in this screen, designated Sprm-1, was used to screen approximately $10^6$ plaques from a rat testis cDNA library. The testis cDNA was generated using random hexamers and was cloned into lambda zap II as previously described (Anderson, supra). Four clones from the testis library were sequenced on both strands using the dideoxy chain termination method as previously described (Anderson, supra). The longest clone from the testis library was 1231 bp long, in agreement with the size of the actual transcript in testis suggesting that the identified cDNA is full length.

The longest cDNA insert contained an initiation codon within a strong Kozak consensus sequence (Kozak, Nucleic Acids Res. 12:857–872 (1984)) 55 bp from the 5' end. The 1008 bp long open reading frame (SEQ ID NO: 3) predicted a 335 amino acid translation product with a molecular weight of 37 kDa (SEQ ID NO: 1). Sprm-1 exhibits considerable homology to Oct-3/4 in the POU-domain and in the COOH-terminus, but no significant homology in the $NH_2$-terminus. There was no homology outside the POU-domain to Oct-3/4-related genes previously described in Hinkley, et al., Mol. Cell. Bio. 12:638–649 (1992); Whitfield, et al., Dev. Biol. 155:361–370 (1993).

Example 2 mRNA Analyses

RNAse protection assays were performed as previously described using 20 micrograms of total RNA and a $^{32}P$-labelled antisense riboprobe representing nucleotides 349 to 786 of the rat cDNA (Yu et al., Cell 67:1251–1266 (1991)). Northern hybridization was performed with a random primed $^{32}P$-labelled Sprm-1 DNA probe comprising nucleotides 349 to 786 of SEQ ID NO: 3. Four micrograms of poly A+ RNA were loaded in each lane. To ensure equal loading the blot was re-hybridized with a beta actin probe as previously described (Yu, V.C. et al., Cell 67:1251–1266 (1991). Similar results were obtained when we used a probe corresponding to the $NH_2$-terminus of Sprm-1 to probe RNA blots (data not shown). In addition, the expression of Sprm-1 only after pubertal maturation indicated that expression occurred in the germ cells as opposed to the somatic cells within the testis.

This analysis revealed a high level of expression in adult testis. In contrast, an extremely low level of expression was found that was near the detection limit of the protection assay, or undetectable, in all other tissues examined. Among these tissues, neonatal skin showed the next highest level of expression after testis. No expression was found in retinoic acid-treated or untreated embryonic carcinoma cell lines (data not shown). Expression in testis was confirmed by a RNA blot with poly A+ RNA from adult testis, neonatal skin and a pituitary somatotroph cell line. A single 1.2 kb transcript was detected in testis, whereas no signal was found in skin, consistent with the estimate that expression in testis is at least 50–100 fold higher than in skin. In addition, no expression was detected by in situ hybridization using 16.5 and 17.5 day old rat embryos (data not shown). The conclusion was that expression of Sprm-1 is highly restricted to adult testis.

Example 3

In-Situ Hybridization

The rat testes were from 60 day old animals. In-situ hybridization studies were done as previously described (Anderson, supra, Awgulewitsch, A., Utset, M. F., Hart, C. P., McGinnis, W. & Ruddle, F. H. (1986) *Nature* 320, 328–335). The probes were $^{35}$S-labelled antisense and sense Sprm-1 riboprobes. At least ten round tubules with each stage of spermatogenesis were evaluated at 400× power and the total number of grains per round tubule was quantified. The results are expressed as a percentage of the tubule with the maximum number of grains. The number of grains over tubules of all stages, except stages IX, XII and XIII, were equal whether sense or antisense probes were used. Thus, expression of Sprm-1 mRNA was limited to these three indicated stages of the cycle of the seminiferous epithelium.

During spermatogenesis in the adult rat, germ cell differentiation advances in highly ordered waves along the long axes of the seminiferous tubule Leblond et al., Ann. N.Y. Acad. Sci. 55:548–573 (1952), Parvinen, Endocr. Rev. 3:404–417 (1982). Therefore, each cross-section of a seminiferous tubule contains a series of concentric cohorts of developing germ cells within which all are at the same stage of development. This arrangement permits classification of seminiferous tubules into 14 stages based on the characteristic morphological appearance and cellular associations of spermatogonia, spermatocytes and spermatids in each stage Leblond et al., Ann. N.Y. Acad. Sci. 55:548– 573 (1952). The in situ hybridization was used in combination with Bouin's fixation and staining of adjacent sections of adult testis, to identify the cell type and the stages of spermatogenesis in which Sprm-1 mRNA was expressed. Expression was limited to a subset (10% to 20%) of seminiferous tubules within the testis, and in positive seminiferous tubules Sprm-1 mRNA was localized to primary spermatocytes. Darkfield and lightfield views of an obliquely cut seminiferous tubule, demonstrated intense signal except for a markedly decreased number of silver grains in the lower right corner (data not shown). This tubule was predominantly in stage XII, except for the lower right region, which was progressing toward stage XIV (data not shown).

Based on analyses of many sections, Sprm-1 mRNA expression was almost entirely limited to seminiferous tubule stages XII and XIII. The only exception was a rare expression pattern in stage IX tubules in which Sprm-1 signal was localized in association with residual bodies along the basal region of seminiferous tubules near Sertoli cells (data not shown). No expression was seen in spermatogonia, secondary spermatocytes, spermatids, Leydig cells, macrophages or other interstitial cells. No signal was detected using sense Sprm-1 riboprobes (data not shown).

On the basis of these experiments, we conclude that Sprm-1 is expressed predominantly in primary spermatocytes during the 36- to 48-hr period of progression through late pachytene and diplotene stages (stages XII and XIII of the cycle of the seminiferous epithelium). These stages are the final steps in germ-cell differentiation before meiosis I (data not shown). This is an unusual pattern of expression because with few exceptions (Cunliffe et al., EMBO J. 9:197–205 (1990)) known transcription factors in male germ cells are predominantly expressed in the postmeiotic phases of spermatogenesis (Erickson, Trends Genet. 6:264–269 (1990)). Results of RNase protection assays with total RNA from rate testes during the first round of spermatogenesis are consistent with the data obtained by in situ hybridization. The onset of Sprm-1 mRNA expression was seen between the second and third week (data not shown), correlating with the onset of meiosis during pubertal development.

Example 4

DNA-Protein Binding Assays

Gel mobility shift assays were performed as previously described (Andersen, supra). Sequences of the $H^+O^+,H^-O^+$ ,$H^+O^-$,HSV oct, pOct, CRH, Ftz, Ubx, PO, Prl 1P and DE2 are previously described (Mathis, J. M., Simmons, D. M., He, X., Swanson, L. W. & Rosenfeld, M. G. (1992) EMBO J.11,2551–2561.) En,5'AAGGGGATCCAAATGTCAATT AAATATCAA-3' (SEQ ID NO: 7); POMC CE2,5'-TCCT-CATTAGTGATATTTACCTCCAAATGC-3' (SEQ ID NO: 8); I12 Oct.5'TTTGAAAATATGTGTAATATGTAAAACATTTTG-3' (SEQ ID NO: 9). Care was taken to ensure that each binding site was labelled to similar specific activity and equivalent amount of labelled site was used in each binding reaction. The Sprm-1 protein was a GST fusion protein purified by glutathione affinity chromatography (Smith, D. B. et al., Gene 67:31–40 (1988). The Pit-1 protein was bacterially expressed as previously described (Ingraham, H. A. et al., Cell 61:1021–1033 (1991)). The Oct-2 protein was in-vitro translated as previously described (Andersen supra.). The SAAB assay was performed as previously described (Blackwell, T. K. & Weintraub, H. (1990) *Science* 250, 1104–1100.). The sequence of the template was: 5'-CGATGAATTCCTAAGC GCATNNNNNNNNGAGCTCAGATCTC-3' (SEQ ID NO:10) (fixed part of site is underlined). The sequences of the primers that were used for amplification of the template were 5'-CGATGAATTCCTAAG-3' (SEQ ID NO: 11) and 5'-ACGAGATCTGAGCTC-3' (SEQ ID NO: 12) (antisense). The conditions for the polymerase chain reaction were as follows: 30 to 35 cycles at 94° C. for 45 sec., 48° C. for 2 min. and 72° C. for 30 sec. The gel-mobility shift conditions were as previously described (Andersen, supra.). The selected template was sequenced after four rounds of selection by the means of a $^{32}$P-labelled sense primer as previously described (Blackwell, Supra.).

POU-domain transcription factors are characterized by a bipartite DNA-binding domain composed of a POU-specific domain linked with variable spacing to the POU homeodomain. Studies of the binding characteristics of Oct-1 and Oct-2 POU-domains have shown that both bind with highest affinity to a sequence containing a core octamer element: 5'-ATGC(A/T)AAT-3' (SEQ ID NO: 13) (Baumruker et al., Genes Dev. 2:1400–1413 (1988); LeBowitz et al., Genes Dev. 3:1625–1638 (1989); Verrijzer et al., Genes Dev. 4:1964–1974 (1990); Kxistie et al., Genes Dev. 4:2383–2396 (1990); Kemler et al., Nucleic Acids Res. 19:237–242 (1991); Aurora et al., Mol. Cell. Biol. 12:455–467 (1992); Verrijzer et al., EMBO J. 11:4993–5003 (1992)), with the POU-specific domain and POU homeodomain contacting the left and right half of the site, respectively (Verrijzer et al., Genes Dev. 4:1964–1974 (1990); Kristie et al., Genes Dev. 4:2382–2396 (1990); Verrijzer et al., EMBO J. 11:4993–5003 (1992)). Because Oct-3/4 protein binds the octamer element with lower affinity than Oct-1 and Oct-2 proteins (Aurora et al., Mol. Cell. Biol. 12:455–467 (1992)), we tested whether Sprm-1 might bind with higher affinity to a series of sites distinct from the octamer site. As controls we tested binding of these same sites to Oct-2 and Pit-1 proteins (data not shown). Sprm-1 has a distinct, although overlapping, binding preference (HSV Oct>CRH>POMC DE2>Ftz=$H^+O^+$>pOct=$H^-O^=$ sites) compared with Oct-2 ($H^+O^+$=$H^-O^+$>pOct>I12 Oct>HSV Oct>CRH) and Pit-1 ($H^+O^+$>$H^-O^+$=HSV Oct= Prl 1P=Ftz>CRH sites). Alignment of the highest-affinity binding sites for Sprm-1 allowed us to derive a consensus sequence: 5'-GCATNN(±N)TAAT-3' (SEQ ID NO: 14) (data not shown). Mutational analyses of the CRH site gave further support for these analyses because mutations in the GCAT and TAAT regions completely inhibited binding, whereas mutations in the variable region had less effect (data not shown). These experiments suggest that Sprm-1 has a preference for sites that are distinct from a classic octamer site. To test this hypothesis we used the SAAB assay (Blackwell et al., Science 250:1104–1110 (1990)) to identify a preferred binding site for Sprm-1. With this assay we identified a preferred site: 5'-GCATATGTTAAT-3' (SEQ ID NO: 15) (selected nucleotides are in bold-face type; data not shown), which is essentially a variant octamer site. This site is highly related to the preferred binding sites for Oct-1 (Verrijzer et al., EMBO J. 11:4993–5003 (1992)) and Bin-5 (Andersen et al., J. Biol. Chem. 268, in press (1993)) proteins. However, because Sprm-1 binds with lower affinity to the immunoglobulin octamer site ($H^-O^+$) than the selected site (data not shown), minor differences in the octamer site and the nucleotides surrounding the core octamer motif appear important for selective high-affinity binding of this POU-domain protein (data not shown; see also Baumruker et al., Genes Dev. 2:1400–1413 (1988), and Kemler et al., Nuc. Acids Res. 19:237–242 (1991)).

Example 5

Generation and Isolation of Sprm-1 Protein

Three different bacterial expression plasmids were generated by cloning DNA fragments encoding amino acids 1–334 (holoprotein), amino acids 1–116 ($NH_2$-terminus) and amino acids 262–334 (COOH-terminus) of the rat Sprm-1 protein into an expression vector pGEX-KG containing an in-frame glutathione-S-transferase coding sequence *E. coli* DH5alpha cultures that had been transformed with these plasmids were grown up. Fusion protein was isolated with glutathione-affinity chromatography in accordance with the procedure set forth in Smith et al., Gene 67:31–40 (1988). In some experiments, the Sperm-1 protein was cleaved from the glutathione-S-transferase molecule by treatment with thrombin.

Example 6

Generation of Sperm-1 Antisera

The three different rat Sperm-1 fusion proteins were isolated using SDS/page gel electrophoresis. These proteins were injected subcutaneously into rabbits followed by serum collection according to standard protocols. Ed Harlow and David Lane: *Antibodies. A Laboratory Manual*, Cold Spring Harbor Laboratory, (1988).

Histochemistry

Rat adult testis were fixed overnight in 10% buffered formalin followed by embedding in paraffin. Sections were analyzed with immunoperoxidase staining according to standard techniques described in Harlow, supra. These experiments revealed stage-specific expression of Sprm-1 protein in spermatids.

Example 7

Isolation of Mouse Sperm-1 Coding Sequence

A mouse S129 genomic DNA library was plated and screened with a radioactively labelled full length rat Sprm-1 cDNA probe according to the procedures disclosed in Andersen et al., Science 260: 78–82 (1993). The portion of the mouse Sperm-1 gene corresponding to the coding region was sequenced on both strands. The mouse genomic DNA sequence is set forth above in SEQ ID NO: 4.

All publications and patent applications mentioned in this specification are indicative of the level of skill of those skilled in the art to which this invention pertains. All of these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appended claims.

---

We claim:

1. An isolated and purified DNA molecule encoding a mammalian Sprm-1 protein or an analog of said mammalian Sprm-1 protein that exhibits Sprm-1 DNA binding activity.

2. The isolated and purified DNA molecule of claim 1, wherein the encoded Sprm-1 protein exhibits the DNA binding activity of the Sprm-1 protein set forth as SEQ ID NO: 1 or the Sprm-1 protein set forth as SEQ ID NO: 2.

3. The isolated and purified DNA molecule of claim 1, which encodes rat Sprm-1 protein set forth as SEQ ID NO: 1.

4. The isolated and purified DNA molecule of claim 3, set forth as SEQ ID NO: 3.

5. The isolated and purified DNA molecule of claim 1, which encodes mouse Sprm-1 protein set forth as SEQ ID NO: 2.

6. The isolated and purified DNA molecule of claim 5, set forth as SEQ ID NO: 4.

7. A recombinant DNA molecule comprising a 5' regulatory region operably linked to the DNA molecule of claim 1.

8. A recombinant DNA molecule according to claim 7, wherein said 5' regulatory region comprises a constitutive promoter.

9. A vector comprising the DNA molecule of claim 8.

10. A host cell stably transformed with the DNA molecule of claim 1.

\* \* \* \* \*

UNITED STATES PATENT AND TRADEMARK OFFICE
CERTIFICATE OF CORRECTION

PATENT NO.  : 5,612,220
DATED       : March 18, 1997
INVENTOR(S) : Andersen et al.

It is certified that error appears in the above-identified patent and that said Letters Patent is hereby corrected as shown below:

Column 1, line 42, "ovalation" should read --ovulation--
Column 4 in table 1, line 21, first appearing "Glu" should read --Tyr--
Column 5 in table 1, line 10, "Try" should read --Trp-- under 170
Column 5 in table 1, line 31, "Try" should read --Trp-- under 260
Column 5 in table 1, line 34, "Try" should read --Trp-- under 260
Column 7 in table 2, line 70, "dTC" should read --GTC-- under 750
Column 7 in table 2, line 72, "ICCA" should read --CCA-- under 780
Column 12, line 12, "[5'oligo:5'TAGAATTCAR" should read --[5'oligo:5'-TAGAATTCAR--
Column 14, line 24, "Oct.5'TTTGAAAATATGTGTAATATGTAAAACATTTTG-" should read -- Oct.5'-TTTGAAAATATGTGTAATATGTAAAACATTTTG---
Column 14, line 59, "Kxistie" should read --Kristie--
Column 15, line 27, "Bin-5" should read --Brn-5--

Signed and Sealed this

Eighth Day of July, 1997

Attest:

BRUCE LEHMAN

Attesting Officer

Commissioner of Patents and Trademarks